Figure 1:
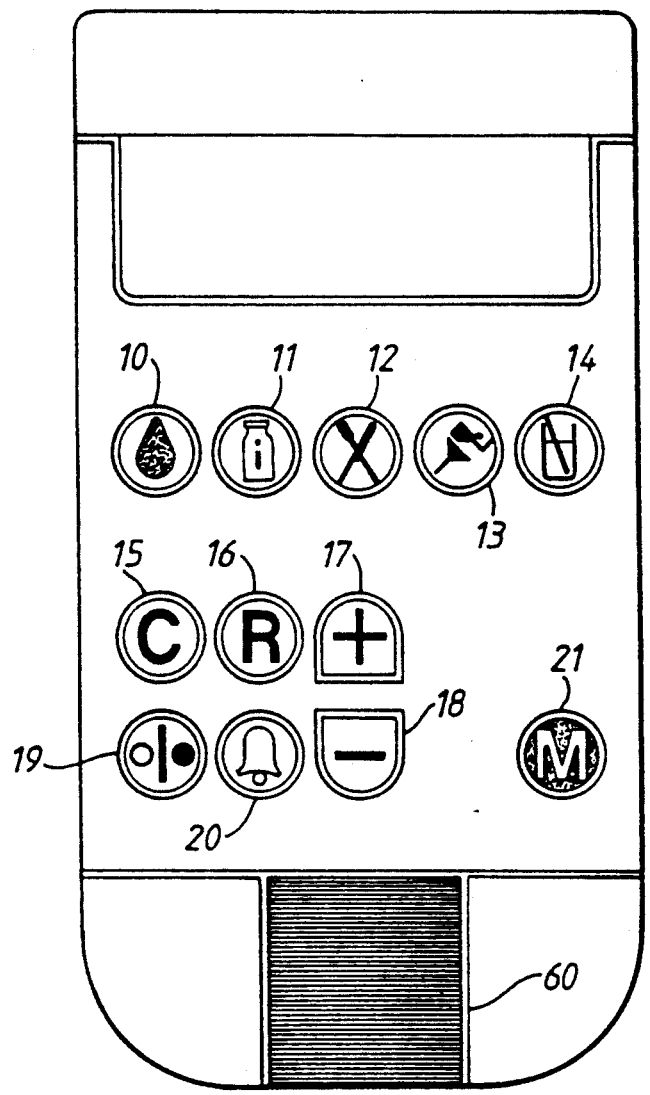

United States Patent [19]

Beckers

[11] Patent Number: 5,216,597
[45] Date of Patent: * Jun. 1, 1993

[54] DIABETES THERAPY MANAGEMENT SYSTEM, APPARATUS AND METHOD

[75] Inventor: Andreas G. F. Beckers, Maastricht, Netherlands

[73] Assignee: Diva Medical Systems bv, Maastricht, Netherlands

[ * ] Notice: The portion of the term of this patent subsequent to May 28, 2008 has been disclaimed.

[21] Appl. No.: 705,916

[22] Filed: May 28, 1991

Related U.S. Application Data

[63] Continuation of Ser. No. 483,582, Feb. 22, 1990, Pat. No. 5,019,974, which is a continuation of Ser. No. 186,477, Apr. 26, 1988, abandoned.

[30] Foreign Application Priority Data

May 1, 1987 [EP] European Pat. Off. ........ 87304029.9

[51] Int. Cl.$^5$ ............................................. G06F 15/42
[52] U.S. Cl. .................... 364/413.02; 356/39
[58] Field of Search ............ 364/413.01, 413.02, 364/413.09, 413.29, 709.02, 710.02, 710.11; 356/39

[56] References Cited

U.S. PATENT DOCUMENTS

| | | | |
|---|---|---|---|
| 4,659,178 | 4/1987 | Kyoguku | 350/166 |
| 4,803,625 | 2/1989 | Fu et al. | 364/413.03 |
| 4,831,562 | 5/1989 | McIntosh et al. | 364/569 |
| 4,853,854 | 8/1989 | Behar et al. | 364/413.01 |

*Primary Examiner*—Gail O. Hayes
*Attorney, Agent, or Firm*—Richard P. Crowley

[57] ABSTRACT

A system and apparatus for efficient medical control of a medical condition such as diabetes comprises a recorder, an interface and a master computer. The master computer develops a programme of therapy which is downloaded into the recorder which then reminds the patient of any therapy due and records that the therapy has been effected. The recorded from the recorder is subsequently fed back to the master computer to improve or alter the therapy programme.

16 Claims, 4 Drawing Sheets

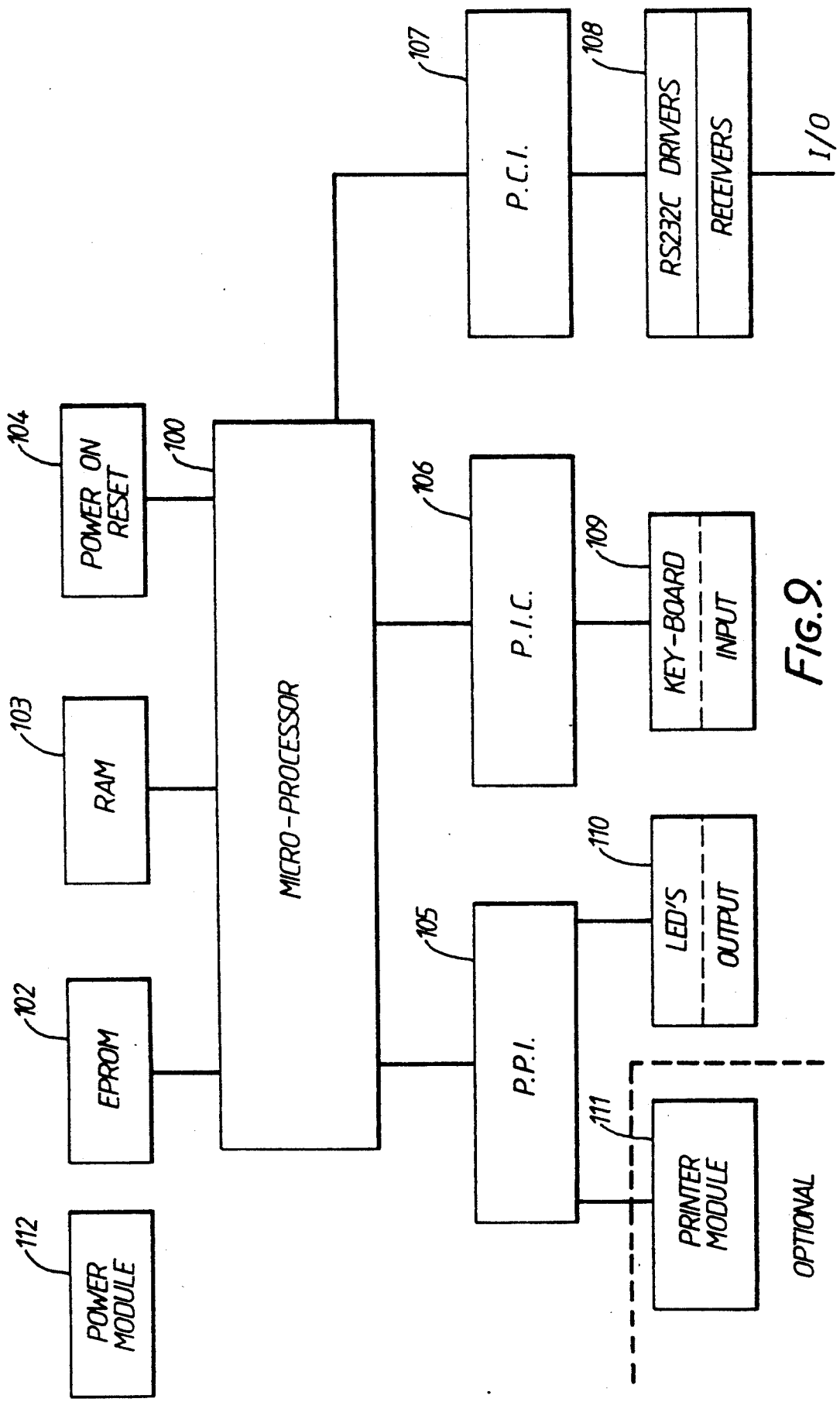

DIABETES THERAPY MANAGEMENT SYSTEM, APPARATUS AND METHOD

This is a continuation of copending application Ser. No. 07/483,582 filed on Feb. 22, 1990, now U.S. Pat. No. 5,018874 which is a continuation of USSN 07/186,477, filed Apr. 26, 1988, now abandoned. Appendices A-C may be found in microfiche form as part of the application file.

This invention is concerned with apparatus for use in a system of outpatient management, i.e. a system for gathering, processing and analysing data to provide for an outpatient an individually tailored programme of treatment or medication.

The system described herein has been specifically designed for the control of diabetes but could be applied to many other conditions requiring outpatient monitoring.

In managing diabetes it is normal to derive for each patient the optimum programme of eating, insulin doses and exercise, the patient then following that programme in the course of their normal daily life and compensating for any departures from the normal programme. There are two major problems inherent in this, namely that the optimum programme is subject to change because of changing age or health of the patient or because of a change in the patient's daily routine, and that any compensation by the patient for a departure from the programme is at best an educated guess.

It is an object of the present invention to provide apparatus in the context of an overall management system that obviates or mitigates these problems.

The present invention is a system of outpatient management comprising a computer into which are loaded details of the patient, or his condition, a monitor in the possession of the patient and an interface, enabling the computer and the monitor to exchange information, the computer being programmed to produce from the loaded monitor patient details a programme of treatment or medication which is recorded in the patient's monitor, the monitor including a computer, a display and a keyboard and being programmed to use the recorded programme to display at appropriate times the desired treatment or medication and to accept and record information entered by the patient on the keyboard.

The present invention is also a monitor for use by a patient in a system of outpatient management, the monitor comprising a computer, a keyboard and a display, the computer being adapted to store a course of medication or treatment, to display at appropriate times the desired medication or treatment and to accept and store keyboard input from the patient relating to the medication or treatment.

The present invention is further apparatus for measuring colour change comprising means for supporting an article subject to colour change, a light source and means for directing light from the source onto the article as a well defined spot, and means for receiving reflected light from the light source and measuring the intensity of the light.

Figure 2:
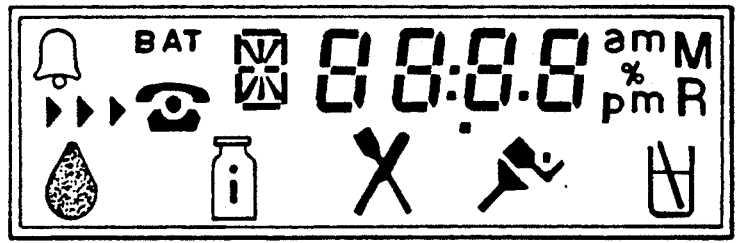
Figure 3:
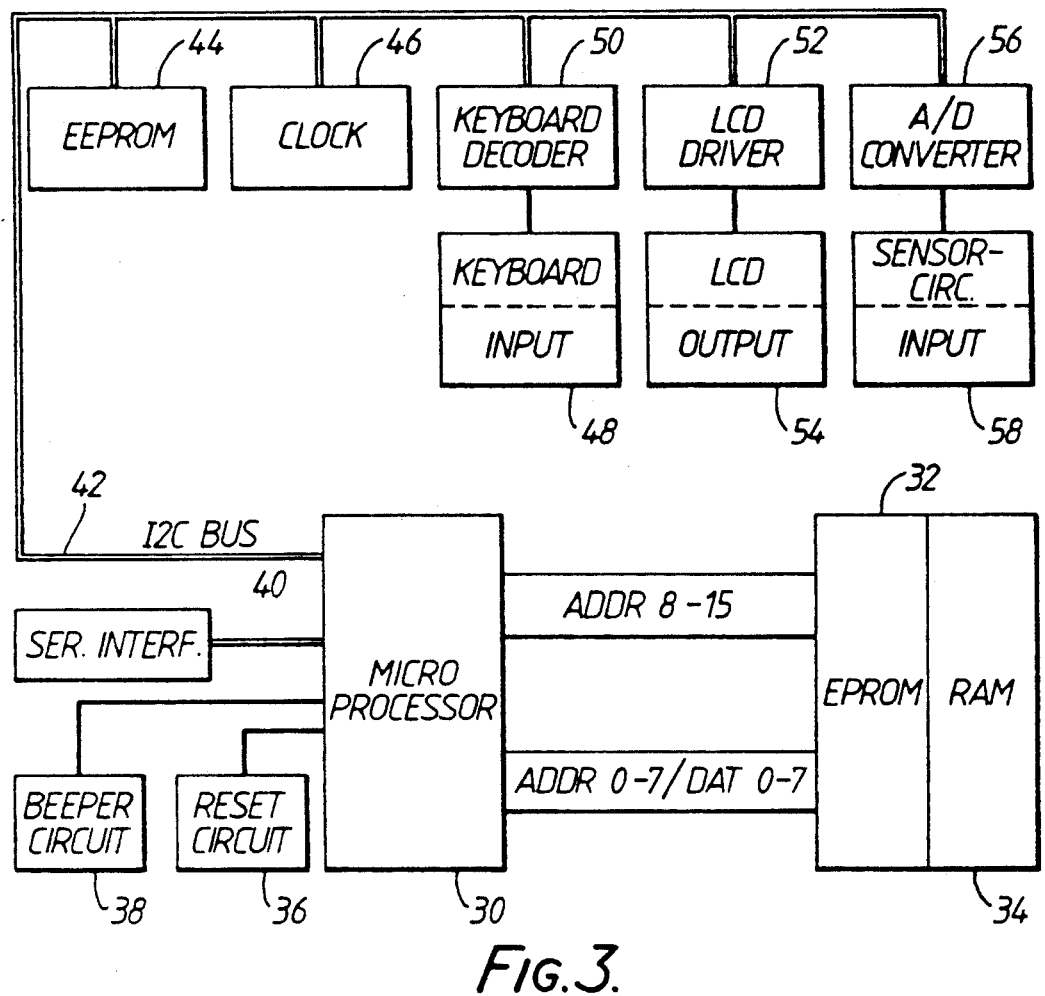
Figure 8:
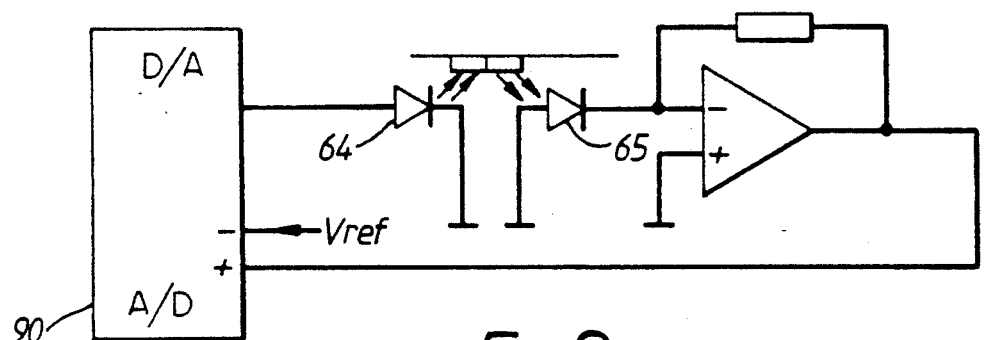
Figure 4:
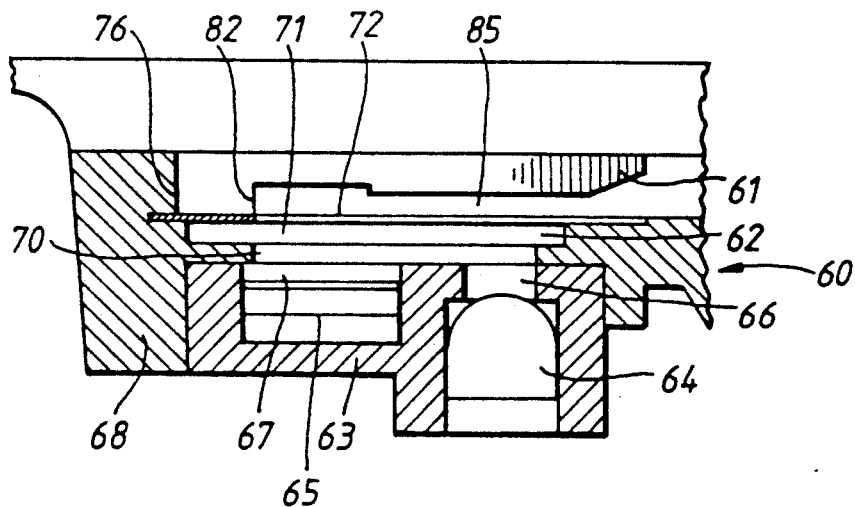
Figure 5:
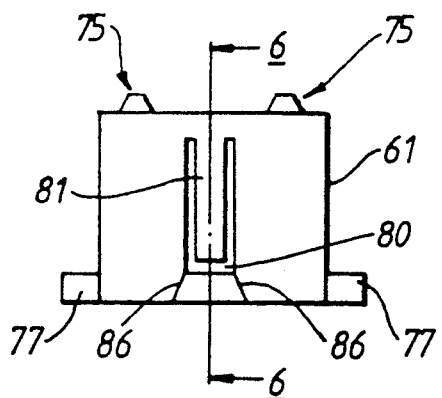
Figure 7:
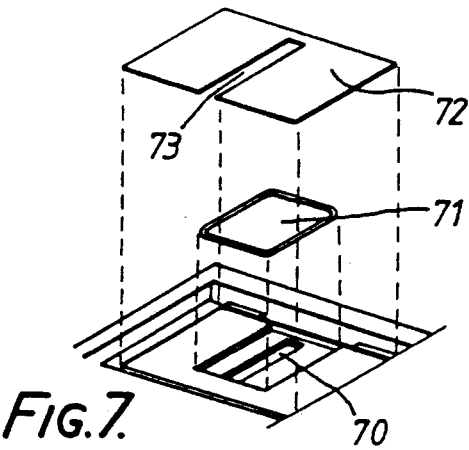
Figure 6:
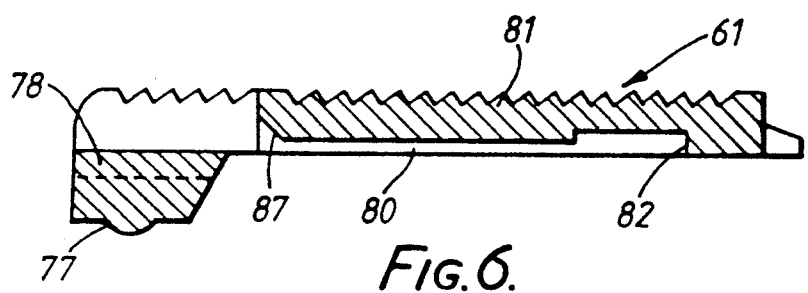

An embodiment of the present invention will now be described by way of example, with reference to the accompanying drawings, in which:

FIG. 1 shows the face of a recorder used by a patient;
FIG. 2 shows the full display of the recorder of FIG. 1;
FIG. 3 is a block schematic diagram of the recorder of FIG. 1;
FIG. 4 is a cross sectional view of a blood glucose strip reader;
FIG. 5 is a plan view of a strip carrier used in the reader of FIG. 4;
FIG. 6 is a cross section on the line 6—6 of FIG. 5;
FIG. 7 is an exploded view of a reflection compartment used in the reader of FIG. 4;
FIG. 8 is a circuit diagram of the blood glucose strip reader; and
FIG. 9 is a block circuit diagram of an interface unit used with the recorder of FIG. 1.

The overall system of diabetes management comprises three elements, namely a patient operated monitor/recorder (hereinafter referred to simply as a recorder), a master computer for developing the optimum programme on the basis of the information recorded by the patient, and an interface unit used to transfer data between the recorder and the master computer or a printer or even a modem.

The master computer is simply a personal computer having a special programme and which is operated by the doctor or medical specialist to develop on the basis of the patient's data the optimum programme for that patient and to insert appropriate instructions into the patient's recorder.

The recorder itself, when the appropriate instructions have been entered from the master computer, prompts the patient to perform the actions according to the programme at the appropriate time. The patient also enters into the memory of the recorder information relating to insulin types and doses, diet, exercise, urine test results, hypoglycemic reactions and special events. The recorder also incorporates a blood glucose test strip reader and automatically stores the measured values in the memory. All the entries in memory are coded and labelled with date and time.

The keyboard of the recorder is illustrated in FIG. 1, the various symbols on the various keys 10 and 21 having the following meaning:

10—Blood Glucose: Starts a procedure enabling read out of BG test strips according to manufacturer's procedure
11—Insulin: Starts a procedure enabling review and/or entry of insulin guidelines
12—Diet: Starts a procedure enabling review and/or entry of diet guidelines
13—Exercise: Starts a procedure enabling review and-/or entry of exercise guidelines
14—Urine Test: Starts a procedure enabling entry of urine test results according to existing methods of urine testing
15—C key: Starts a procedure enabling clearing or zero setting of the values in the display, preventing memory storage of displayed values, and enabling clock-/calender setting
16—R key: Starts a procedure enabling restoration of preset values, review of previous entered BG values, and recall of previous preset guidelines
17—+key: Enables the increase of values displayed and the recording of special events
18——key: Enables the decrease of values displayed and recording of hypoglycemic reactions
19—on/off key: Enables on/off switching of the Romeo
20—bell key: Switches alarm on or off
21—M key: Starts procedure enabling to store the various displayed data into the recorder's memory.

The monitor/recorder also has an LCD as shown in FIG. 2, the various symbols having the following meaning:

= Blood Glucose function active
= Insulin function active
= Diet function active
= Exercise function active
= Urine test function active
= Alarm enabled
PM/AM = Time indicators
= Memory full up indicators
= Appointment time/Consult physician indicator
% = Percent indicator
= Alpha Numeric digit
= Numeric digit
: = Seconds indicator
. = Floating point
BAT = Battery Low indicator
M = M key operation
R = R key operation In FIG. 3 is shown a block schematic diagram of the recorder.

The entire recorder operates under the control of a standard 80 C31 microprocessor 30 which, besides its internal memory is provided with external memory in the form of a 32 kb EPROM 32 and an 8 kb RAM 34. A reset circuit 36, to which is connected the ON/OFF key 19, functions to provide a proper startup reset for the system, to block an accidental reset during normal system operation, and to generate an interrupt instead of a reset to shut the system down via the ON/OFF key 10. The beeper circuit 38 is a simple 4.6 KHz beeper which provides audible alarm signals under the control of the microprocessor 30, while the serial interface 40 is the standard serial interface and is used to interface the system with the interface unit.

All the other components of the system are connected to, and controlled by, the microprocessor 30 by a two wire serial bus 42. The EEPROM memory 44 is divided into two parts, in one of which is stored the patient therapy information such as insulin injection times and amounts, blood glucose measurement times, diet meal times and amounts, exercise times and duration. The other part of the EEPROM is used as a memory buffer to store the results of the last 85 blood glucose measurements, thus allowing the patient to review his blood-sugar count over a period of time. As this memory is an EEPROM, the stored data is not lost in the event of a total power loss.

The clock circuit is a PCF8573 integrated circuit suitable for serving the bus 42. The keyboard 48 comprises the key shown in FIG. 1 with the exception of the ON/OFF key 19 which, as previously noted, is connected directly to the reset circuit 36. Associated with the keyboard is a keyboard decoder 50 which comprises an integrated circuit able to read and drive the keyboard circuit.

The LCD 54 is shown in detail in FIG. 2 and has a driver circuit 52. The sensor circuit 58 with an associated A/D converter 56 are used for blood glucose measurements and will be described in more detail later.

The operation of the display and the key board for the various functions is as follows:

INSULIN THERAPY

At the programmed time an internal, audible alarm goes off and repeats after one minute.

The patient turns on the recorder by pressing "ON/OFF" key 19 and the display shows the actual time, the alarm symbol (if selected) and the insulin therapy symbol, the insulin symbol and the dots in time blinking slowly.

When the patient presses the insulin key 11, the insulin symbol in the display stops blinking, the insulin type and number of units appear in the display.

After four seconds, the "+" symbol appears in the alphanumeric field and then, in the case of a mixed shot, the second type and number of units appear in the display.

INSULIN THERAPY FOLLOW UP

When the patient has taken the correct dose of insulin, he presses the red M-store key 21 to confirm this fact.

In the display the first insulin type and dose is redisplayed followed by "+" and then the second insulin type and dose in case of a mixed shot. This scroll is done once. Simultaneously "M" appears in the display, together with insulin symbol.

During memory record, the memory may be cleared by pressing the "C" key 15.

After the therapy has been scrolled once, the actual time shows up in the display and insulin symbol vanishes.

INSULIN THERAPY DEVIATION

If the patient wishes to adjust the amount of insulin, he presses the insulin key 11 and the first insulin type and dose appears in display. The patient can then press the "+" key 17 or the "−" key 18 to increase or decrease the insulin units.

If there is a second type of insulin (i.e. a mixed shot) the insulin key 11 can be pressed again and the dose adjusted in the same way as above.

When the dose has been taken, the red "M" key 21 is pressed to confirm and store the adjusted therapy. The display confirms "adjusted" therapy by scrolling adjusted therapy once, displaying solid insulin bottle and "M" for memory record. The display then returns to actual time display.

The "C" key 15 can always be used to clear numbers currently being displayed. This mode is identical to normal calculator operation. To return to the prescribed therapy after deviation, patient presses the "R" key 16.

DIET THERAPY

The diet therapy may be operated in any one of three ways:
A. Diet exchange system: individually selected exchanges per meal.
B. Diet indication system requiring an entry indicating:
   above normal diet "+" key 17
   normal diet "R" key
   below normal diet "−" key 18
C. Diet "YES/NO" system requiring an entry indicating:
   diet followed "M" key 21
   diet skipped "C" key 15.

PROCEDURE FOR DIET EXCHANGE

The procedure is essentially the same as for the insulin therapy. At the programmed time the audible alarm sounds and is repeated after one minute. The patient turns on the monitor/recorder by pressing the "ON/-

OFF" key and the display shows the actual time, the alarm signal (if selected) and the diet therapy signal. The diet symbol and the dots in time blink slowly.

When the patient presses the diet key 12, the diet symbol stops blinking and the programmed therapy is displayed. In the present invention the programmed diet therapy can be any one of eight possibilities of which six are standard and two can be designed by the doctor.

DIET THERAPY FOLLOW UP

This is essentially the same procedure as was described for insulin. After completing the therapy the red "M" key 21 is pressed to record the fact, the diet therapy scrolls once while "M" appears in the display with a steady diet symbol. Thereafter the actual time shows in the display.

DIET THERAPY DEVIATION

The therapy can be adjusted by means of the "+" and "−" keys as described for insulin therapy.

PROCEDURE FOR DIET INDICATION AND DIET YES/NO SYSTEMS

The procedures for these possible systems (the initial choice being made by the master computer) is essentially the same as described above, the difference being that in the diet indication system the patient must enter whether the food eaten is above, below or equal to the normal programmed diet, and in the diet YES/NO system the patient must indicate whether the diet was followed or skipped.

EXERCISE THERAPY

This may be programmed in any one of three ways.
A. Specific exercise system with individually selected exercise level and duration, set in the master computer and downloaded to the recorder.
B. Exercise indication system requiring entry indicating:
   more exercise "+" key
   normal exercise "R" key
   less exercise "−" key.
C. Exercise "YES/NO" system requiring entry indicating:
   exercise done "M" key
   exercise skipped "C" key.

PROCEDURE

The procedure for exercise therapy is essentially the same as for the therapies previously described.

URINE TESTING

The master computer will programme the monitor/recorder in one of four ways, viz:
if this function is used at all
if only ketones function is used
if only urine glucose is used
if both ketones and urine glucose are used.

Any test strip can be used as the patient has always to make a manual entry for this function. The master computer must be informed of the type of strip (s) being used and the appropriate coding.

PROCEDURE

The procedure followed by the patient is essentially the same as previously described except that the patient must enter the results of the test. In the case of the urine ketone function a negative test result is recorded by use of the "−" key 18 while a positive test result is recorded by use of the "+" key 17 once, twice or three times.

In the case of the urine glucose function, the "−" key 18 is used to record a negative result while the "+" key 17 is used up to eight times to record the possible urine glucose % values as follows: less than 0.1, 0.1 to 0.5, 0.5 to 1.0, 1.0, 1.0 to 2.0, 2.0 to 3.0, 3.0 to 4.0, 4.0 to 5.0, 5.0 to 9.9, and greater than 9.9.

BLOOD GLUCOSE MEASUREMENT

This measurement is effected automatically by a reader in a special compartment in the recorder which will be described in more detail later.

PROCEDURE

The procedure commences with the sounding of the alarm and the normal response by the patient of pressing the "ON/OFF" key 19, the therapy key (blood glucose 10) and inserting a clean test strip into the compartment. The therapy key is again depressed. This allows the recorder to obtain a standard or base reading. Thereafter the patient using the strip from the compartment proceeds with the test by pricking his finger, blotting it on the test strip, and pressing the blood glucose key 10. The recorder then counts for 60 seconds giving audible warnings for the last few seconds to enable the patient to clean the strip at 60 seconds. The recorder continues to count to 120 seconds and gives audible warnings from 115 seconds to enable the patient to insert the strip into the special compartment.

The subsequent measurement of the blood glucose value and the entry of the measured value into memory is automatic.

EVENT MARKERS

An event marker is an additional entry made on the initiative of the patient to record significant events such as
"+" & BG keys hyper
"+" & "diet" keys illness
"+" & "exercise" keys stress
"+" & "insulin" keys fever
"+" & "urine" keys alcohol

RECALL FUNCTION

The recall function enables the patient to go back to an earlier therapy step and store the corresponding activity so long as there is no same therapy alarm active.

RECALL ROUTINE

The patient turns on the recorder and presses the "R" key 16 and then the desired therapy key. The recorder then goes back one therapy in time to an unrecorded blank therapy step and displays the programmed time of that step. The patient can then either accept that time by pressing the therapy key again or can adjust the time to the time at which the therapy took place.

THE BLOOD GLUCOSE TEST STRIP READER

The blood glucose test strip reader 60 is illustrated in FIG. 4 and is located in the middle of the bottom edge of the recorder. The reader 60 consists of three superimposed parts, viz. the strip carrier 61 which positions the BG test strip correctly in the light path, the reflection compartment 62 which defines the light compartment, and an emitter/sensor unit which transmits and receives the light.

The emitter/sensor unit comprises a housing 63 in which are located a light emitting diode 64 having a light intensity output at 565 nM and a photodiode 65 sensitive to the green light of that wavelength. Above each of the diodes 64 and 65 is located an aperture, 66 and 67 respectively, allowing light to pass to and from the reflection compartment, the aperture 66 being formed so that the light from the LED 64 emerges from the housing 63 as a narrow high intensity beam. The housing 63 is accurately located in the main body 68 of the recorder so that the diodes are accurately located relative to the reflection compartment and the strip carrier.

The reflection compartment (see FIGS. 4 and 7) comprises a calibrated slit 70 immediately above the housing 63, a glass 71 which has an antireflection coating with optimum light transmission at 565 nM, and a strip support 72 having a slit 73 above the calibration slit 70. The support 72 serves to space the bloody test strip from the glass 71.

With this arrangement of the reflection compartment above the emitter/sensor unit it can be seen that a strip, accurately located on the support 72 above the slit 73 has fixed spatial relationship with the diodes 64 and 65. It is the purpose of the strip carrier to ensure accurate location of the strip.

The strip carrier 61 as seen in FIG. 5 is essentially a square cover provided with two positioning tongues 75 at its inner edge, the tongues being tapered in two directions to cooperate with two similar cavities 76 in the main body 68 of the recorder thereby to locate accurately the inner edge of the carrier in the recorder. The outer edge of the carrier is provided with clamps 77 which have upper surfaces 78 spaced below the main part of the carrier. The carrier 61 is slid horizontally into position, guide rails (not illustrated) on the main body 68 of the recorder engaging its lateral sides. When fully in position the upper surfaces 78 of the clamps engage the bottom surface of the rails thus securely and accurately locating the strip carrier 61 in the recorder body 68.

The strip carrier 61 is provided with a slit 80 whose width is the same as that of a blood glucose test strip. A cantilevered tongue 81 overlies the main part of the slit 80, extending outwardly from the inner end wall 82 of the slit 80. The tongue 81 is thinner than the main body of the carrier so that a gap 85, substantially equal to the thickness of a test strip, is provided between the bottom of the tongue 81 and the upper surface of the strip carrier 71. To assist in locating a test strip in the gap 81 the side walls of the slit 80 have inclined lead-in portions 86 and the underside of the tongue 81 is formed as a lead-in ramp 87.

When the test strip reader is assembled as shown in FIG. 4, a test strip is inserted into the slit 80 beneath the tongue 81 and when the end of the strip abuts the end wall 82 of the slit 80 the active portion of the strip is located above the diode 64 to be illuminated thereby, light reflected from the active portion being detected by the diode 65.

As seen in FIG. 8 the light emitting diode 64 is energised from the D/A section a D/A-A/D converter 90, the output from the photodiode 65 passing to an operational amplifier whose output is connected back to the The voltage difference between the input and output of the amplifier is converted into a blood glucose value according to a blood glucose conversion table loaded in the EEPROM of the device. This procedure is performed during the base reading of a clean test strip and during measurement of the blood glucose as described in the Procedure section. converter 90.

OTHER FUNCTIONS

The recorder also functions to remind a patient that a consultation with the doctor is due by displaying the telephone symbol, that the memory is getting full by displaying the memory full up symbols, and that the battery is becoming exhausted by displaying the battery low symbol.

SOFTWARE

The recorder operates under the supervision of a terminal software programme stored in the 32K EPROM and the recorder's operation is determined by a software profile downloaded into the EEPROM.

The terminal software consists of the following sections:
a) blood glucose test strip sensor response conversion
b) microprocessor soft control
c) LCD soft driver
d) keyboard encoder/decoder
e) data compression
f) diagnostics
g) power control The software profile consists of the following sections:
a) key function: defines if the keys are operational or not
b) key reaction: defines what action follows activation of a particular key
c) guidelines: defines alarm times, insulin doses and types diet specifications and exercise specifications
d) sensor setting: defines which blood glucose test strip can be used in the corresponding response curve.

The data compression techniques employed are designed to save storage space by a coding system which uses parts of a single byte to refer to different aspects of a therapy. For example in insulin therapy the following coding is used:

| DIABETIC DATA STORAGE -INSULIN- | | | |
|---|---|---|---|
| A | PRESCRIPTION FOLLOW UP | | |
| | 001YYY00 | 001 | =INSULIN CODE |
| | | YYY | =SHOT NUMBER |
| | | 00 | =FOLLOW UP CODE |
| B | TIMING DEVIATION | | |
| | 001YYY01 | 001 | =INSULIN CODE |
| | | YYY | =SHOT NUMBER |
| | | 01 | =TIMING DEVIATION CODE |
| | MMMMMMMM | MMMMMMMM | =0-239 UNITS OF 6 MIN. |
| C | TIMING AND THERAPY DEVIATION | | |
| | 001YYY10 | 001 | =INSULIN CODE |

-continued

| DIABETIC DATA STORAGE -INSULIN- | | |
|---|---|---|
| | YYY | =SHOT NUMBER |
| | 10 | =TIMING & THERAPY DEVIATION CODE |
| MMMMMMMM | MMMMMMMM | =0-239 UNITS OF 6 MIN. |
| DDDDDDDD \|f\| OR \|f\| OR \|m\| | DDDDDDDD | =INSULIN DOSE |
| DDDDDDDD \|m\| OR \|l\| OR \|l\| | | 0-253 * 0.5 UNITS |
| D ADDITIONAL ENTRY | | |
| 00100011 | 001 | =INSULIN CODE |
| | 00011 | =ADDITIONAL ENTRY CODE |
| MMMMMMMM | MMMMMMMM | =0-239 UNITS OF 6 MIN. |
| DDDDDDDD \|f\| OR \|f\| OR \|m\| | DDDDDDDD | =INSULIN DOSE |
| DDDDDDDD \|m\| OR \|l\| OR \|l\| | | 0-253 * 0.5 UNITS |

A similar pattern is used for the other therapies available—the first three bits of the byte defining the therapy, the second three defining the therapy number and the last two indicating the number of relevant bytes to follow.

A full programme listing for the recorder is included in Appendix A hereto, and the software documentation is included in Appendix B.

INTERFACE

Introduction

As previously discussed the recorder is used with an interface unit to enable data to be transferred between the recorder and the master computer. The recorder simply plugs into the interface which in turn plugs into the master computer or a modem. Alternatively the data can be printed out on a printer which can be incorporated in the interface.

Referring to FIG. 9, the interface comprises the following components.

Blocks 100, 102 and 103

These blocks contain the common known microcontroller components such as a microprocessor (100), address-latches (102) and a static ram (103).

Block 104

When the interface is switched on, this module provides a reset for the microprocessor in order to read out the program-memory from the proper start address.

Block 105

With the programmable Peripheral Interface (P.P.I.) it is possible to connect a thermal printer to print out diabetic data. This integrated circuit has three parallel I/O ports. Two are used for the optional printer. The third part is used for indication of the present mode for which LED's are used. Every time only one LED lights up next to a symbol to indicate this mode.

Block 106 The programmable Interrupt controller (P.I.C.)

Handles several interrupts generated by other peripherals such as the keyboard or the serial-communication port which is described in Block 107. On its turn the P.I.C. generates an interrupt which is sent to the microprocessor.

If the microprocessor receives an interrupt the controller is checked for the origin.

Block 107

The Programmable Communications Interface (P.C.I.) provides together with Block 108 the serial communication with a computer. The P.C.I. can be programmed to communicate at several baud-rates.

For direct communication with a computer 9600 baud is used.

It is possible to connect a modem to this port in order to communicate over long distances. The transmission speed is selectable: 1200 baud or 300 baud.

Block 108

This block contains the drivers and receivers to transform T.T.L. to V.24 levels and vice versa.

Block 109

The key-board has three push-buttons. They have special symbols according to their function.
:Scrolling through the several modes.
:Actual start of the operation.
:Paper feed (with printer option).

Block 110

The mode indications are listed below.
Print-out of blood-glucose values in graphic and in list format.
Print-out of insulin values in graphic and in list format.
Print-out of diet exchange values in graphic and in list format.
Print-out of exercise values in graphic and in list format.
Print-out of summary of the last seven days recording.
Therapy listing.
Phone-modem communication at a speed of 1200 baud.
Phone-modem communication at a speed of 300 baud.
Direct communication with a computer at a speed of 9600 baud.

Block 111

An optional printer-box can be inserted. For the possible print-outs see above.

Block 112

The interface is powered by an external transformer. (220/110 V to 2×6 V).

Within the interface this voltage is stabilized to the several necessary voltage-levels.

The communication between the recorder and the interface is realized by a 6 pins connector, which is connected to the serial port of the microprocessor.

A full programme listing for the interface is provided in Appendix C.

I claim:

1. A system for outpatient treatment management for diabetes, the system which comprises:
   a) a master computer means programmed to develop on the basis of the input data of an individual patient, including blood glucose, food intake, insulin dosage and exercise, analyzed with respect to that individual patient's diabetic condition, the optimum program of treatment including insulin medication, diet and exercise for that patient, such optimum treatment options which are adjustable by that patient responsive to input of therapy information entered by that patient received from the portable monitor via an interface means;

b) a portable monitor means;

c) interface means including an interface display means to enable the master computer means and the portable monitor means to exchange information, to read the instructions stored in the portable monitor means and to display on the interface display means graphically or numerically selected patient therapy information periodically on command of the patient;

d) the portable monitor means comprising:

i) monitor display means for displaying treatment therapy guidelines to the patient;

ii) a keyboard including action key means for accessing selected therapy guidelines stored in the portable monitor means for making entries and for identifying treatment options available to the patient including time periods for said treatment options and including operating key means for varying entries stored on the portable monitor means;

iii) a programmed computer into which patient therapy information is entered by the patient's use of the keyboard and action key means which is adjusted by the patient by keying in changes after consulting display of graphical or numerical information without access to the main computer means or consultation with a physician;

iv) portable storage means for accepting and storing patient treatment instructions including guidelines for treatment therapy for that individual patient from the master computer means;

v) blood glucose test means to measure automatically the blood glucose value of the patient;

vi) monitor therapy storage means for accepting patient therapy information entered by the patient's use of the keyboard and action keys means and test results including blood glucose values automatically measured by a blood glucose test means for access by the patient's use of the keyboard;

vii) the programmed computer of the portable monitor means comprising 1) means to display on the monitor display screen at the appropriate times the guidelines for patient therapy from the storage means providing instructions relative to the desired treatment options or medication dose for that individual patient to prompt the patient to perform the displayed information at the appropriate time and to provide for selection of variations of therapy for medication, diet and exercise with options for deviations responsive to periodic displays provided by the interface display means;

2) means to accept and store in the monitor therapy storage means the prompted patient therapy information entered by the patient including adjustments based upon the guidelines selected by the patient on the keyboard on a periodic basis based on information as to the patient's own selected therapy including deviations from the preexisting schedule of treatment pursuant to the guidelines and;

3) means to display past patient therapy measurements over a period of time as desired by the patient.

2. A system as claimed in claim 1 in which the portable monitor means is programmed to retrieve the details of the optimum program of desired treatment options for therapy or medication dose for that individual patient directly from the monitor therapy storage means within the portable monitor means which previously received the information of such optimum treatment options for therapy and medication from the master computer means.

3. A system as claimed in claim 1 in which the portable monitor means is programmed to retrieve the details of calender dates of medical tests due directly from storage means within the monitor and displays from the recorded program of the master computer means that a medical test is now due and records the test results accepted by the monitor storage means entered by the patient on the keyboard.

4. The system as claimed in claim 1 in which the blood glucose means comprises means to determined the blood glucose value of the patient from a test strip and means to store present and past blood glucose values.

5. A system as claimed in claim 1 in which the blood glucose test means comprises:

a) a means for supporting a blood glucose test strip subject to color change;

b) a light source and means for directing light from the source onto the article as a well defined spot;

c) a means for receiving reflected light from the light source;

d) a means for measuring the intensity of the light to determine the blood glucose value of the patient; and e) means for automatic storage of present and past glucose measurements.

6. The system as claimed in claim 5 wherein the blood glucose test means includes an optical filter located between the strip and the light source and having optimum transmission at the dominant wavelength of the light source.

7. The system as claimed in claim 1 wherein the monitor display means and the keyboard include symbol means for identifying types of therapy being accessed comprising a blood glucose therapy symbol, an insulin therapy symbol, an exercise therapy symbol, diet therapy and a urine therapy symbol.

8. The system as claimed in claim 1 which includes:

means for retrieving recorded patient therapy information from the interface means on a regular, periodic basis and revising the optimum program of treatment responsive to the recorded patient therapy information by keying in changes on the keyboard by use of action keys means and operating keys.

9. The system as claimed in claim 1 wherein the interface display means comprises a document display for displaying patient treatment information to permit the patient to select variations to the optimum program.

10. A method of treating a patient having a medical condition which method comprises:

a) deriving a program of treatment from patient information and medical condition including diet, exercise and insulin including pre-stored guidelines for diabetic therapy which permit the patient to make alterations in therapy by using the guidelines without the necessity of connecting back up to a central computer;
b) providing the patient with a portable monitor means comprising a computer having a memory, a monitor display means and a keyboard means for accessing pre-stored guidelines comprising action keys;
c) loading the program into the computer to display on the monitor display means at appropriate times the desired treatment or medication including guidelines for blood glucose therapy, insulin therapy, diet therapy, exercise therapy and urine therapy;
d) recording in the computer memory information of treatment or medication received by the patient, entered by the patient by use of the keyboard means in response to the display of pre-stored guidelines for a treatment or medication which prompts the patient to enter the information at the appropriate time by use of the keyboard means;
e) retrieving the recorded information;
f) revising the program of treatment or medication in light of the information recorded and the pre-stored guidelines provided;
g) reading the information stored in the monitor means and providing a display on command of the patient of selected patient therapy information;
h) displaying at appropriate times to the patient information from the program including guidelines relative to the desired treatment options for medication therapy, diet therapy and exercise therapy for that patient to prompt the patient to perform the displayed information at the appropriate time and to provide options for deviations responsive to information provided by the interface means.

11. The method of claim 10 which includes recording in the computer memory and displaying present or past stored information of the patient.

12. The method of claim 10 which includes displaying the selected patient therapy information on a printout tape.

13. The method of claim 10 which includes:
a) determining the blood glucose value of the patient; and
b) recording in the computer memory and displaying on request of the patient the past or present blood glucose test values.

14. A method as claimed in claim 10 in which the information contained in the display further includes indications that blood glucose and urine tests are due as well as blood glucose therapy information, insulin therapy information, diet therapy information, exercise therapy information and urine therapy information.

15. A method as claimed in claim 10 wherein the monitor includes a blood glucose test means to measure automatically the blood glucose value of the patient from a test strip and which method includes:
a) submitting by the patient of a test strip to determine the blood glucose value of the patient; and
b) recording to the computer memory and displaying on request of the patient the present or past blood glucose test values of the patient.

16. A system of outpatient treatment management of diabetes, which system comprises:

a) a master computer programmed to receive input as to patient diabetic-related information to develop and to revise periodically on the basis of subsequent data of a patient received from a portable monitor the optimum program of diabetic treatment including patient therapy and medication information for the patient and to load individualized instructions of diabetic treatment into the portable monitor to be stored;
b) computer storage means for storage individual patient data inputted and for storing subsequent input data received from the monitor;
c) analyzing means for comparing individual patient data with previous individual patient data stored in the master computer with the said optimum program and for changing the optimum program of treatment responsive to subsequent input data including patient therapy information for the patient on a periodic basis;
d) the portable monitor in the possession of the patient;
e) interface means for enabling the master computer and the portable monitor to exchange information and for displaying on an interface display means individual summary patient data or graphical information to provide the patient with a bases for variation in therapy and medication;
f) the monitor comprising:
  i) a monitor display means to display information to the patient;
  ii) a keyboard;
  iii) a programmed computer into which computer treatment information is entered by the patient's use of the keyboard;
  iv) storage means for accepting and storing patient treatment information from the master computer;
  v) monitor storage means for accepting patient therapy information entered by the patient's use of the keyboard and blood glucose values measured by the blood glucose test means;
  vi) a blood glucose test means to measure the blood glucose value of the patient;
  vii) the monitor computer being programmed;
    1) to display at appropriate times to the patient from the storage means information relative to the desired treatment or medication dose to prompt the patient to make an election of treatment or therapy and to perform the displayed information at the appropriate time;
    2) to accept and store in the monitor storage means the prompted information entered by the patient on the keyboard to include the automatic storage of present blood glucose measurements from the blood glucose test means; and
    3) to display guidelines for medication, diet and exercise, with change options and to permit the patient by use of the keyboard to select variations to the guidelines on a periodic basis;
  viii) monitor display means for displaying treatment guidelines with change options to permit the patient to select by use of the key means variations to optimum guidelines available on a periodic basis; and
g) key means included in the keyboard for recording or processing patient treatment information selected by the patient in the monitor therapy storage means from a plurality of individualized choices.

* * * * *